United States Patent
Beaudry

(10) Patent No.: US 11,123,154 B2
(45) Date of Patent: *Sep. 21, 2021

(54) METHOD AND SYSTEM FOR DETECTING LOCATION OF FIXED WIRELESS ASSET IN A HOSPITAL ENVIRONMENT

(71) Applicant: CareFusion 303, Inc., San Diego, CA (US)

(72) Inventor: Serge Beaudry, St-Lambert (CA)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/752,432

(22) Filed: Jan. 24, 2020

(65) Prior Publication Data
US 2020/0155268 A1 May 21, 2020

Related U.S. Application Data

(63) Continuation of application No. 16/036,739, filed on Jul. 16, 2018, now Pat. No. 10,548,686, which is a
(Continued)

(51) Int. Cl.
*A61B 90/98* (2016.01)
*G06F 16/29* (2019.01)
(Continued)

(52) U.S. Cl.
CPC .............. *A61B 90/98* (2016.02); *A61B 90/90* (2016.02); *G06F 16/29* (2019.01);
(Continued)

(58) Field of Classification Search
CPC ........ A61B 90/98; A61B 90/90; G16H 40/20; G16H 10/40; G16H 10/60; G16H 40/40;
(Continued)

(56) References Cited

U.S. PATENT DOCUMENTS 6,287,252 B1 9/2001 Lugo
6,333,690 B1 12/2001 Nelson et al.
(Continued)

FOREIGN PATENT DOCUMENTS

| KR | 1020090032349 | 4/2009 |
| KR | 1020110008965 | 1/2011 |
| WO | WO-2006076498 | 7/2006 |

OTHER PUBLICATIONS

European Office Action for Application No. 12841989.2, dated Jan. 2, 2017, 9 pages.
(Continued)

*Primary Examiner* — Kerri L McNally
(74) *Attorney, Agent, or Firm* — Morgan, Lewis & Bockius LLP

(57) ABSTRACT

A system is disclosed for determining the location of fixed wireless assets (FWAs). The system includes at least one FWA having an asset tracking number, at least one mobile device wirelessly coupled to the FWA via a first communication link. The mobile device is assigned to one of these people. The system also includes a computer that is coupled to the FWA via a second communication link and to a database. The FWA is configured to forward the data received from the mobile device to the computer along with the FWA's asset tracking number. The computer is configured to determine the location of the FWA based at least in part on the data received from the FWA and the information retrieved from the database.

20 Claims, 6 Drawing Sheets

Related U.S. Application Data continuation of application No. 15/255,852, filed on Sep. 2, 2016, now Pat. No. 10,022,201, which is a continuation of application No. 14/579,355, filed on Dec. 22, 2014, now Pat. No. 9,439,734, which is a continuation of application No. 13/277,033, filed on Oct. 19, 2011, now Pat. No. 8,917,173.

(51) Int. Cl.

| | |
|---|---|
| *G06F 16/9537* | (2019.01) |
| *H04W 4/029* | (2018.01) |
| *G06Q 10/08* | (2012.01) |
| *G16H 10/60* | (2018.01) |
| *G16H 40/20* | (2018.01) |
| *G16H 40/63* | (2018.01) |
| *G08B 1/08* | (2006.01) |
| *A61B 90/90* | (2016.01) |
| *G16H 10/40* | (2018.01) |
| *H04W 4/33* | (2018.01) |
| *G16H 40/40* | (2018.01) |
| *H04L 29/08* | (2006.01) |

(52) U.S. Cl.
CPC ....... *G06F 16/9537* (2019.01); *G06Q 10/087* (2013.01); *G08B 1/08* (2013.01); *G16H 10/40* (2018.01); *G16H 10/60* (2018.01); *G16H 40/20* (2018.01); *G16H 40/40* (2018.01); *G16H 40/63* (2018.01); *H04W 4/029* (2018.02); *H04W 4/33* (2018.02); *H04L 67/12* (2013.01)

(58) Field of Classification Search
CPC ........ G16H 40/63; H04W 4/33; H04W 4/029; G06F 16/9537; G06F 16/29; G06Q 10/087; G08B 1/08
USPC .................................................. 340/539.13
See application file for complete search history.

(56) References Cited

U.S. PATENT DOCUMENTS

| | | | |
|---|---|---|---|
| 6,375,612 B1 | 4/2002 | Guichon et al. | |
| 8,130,093 B2 | 3/2012 | Mazar et al. | |
| 8,228,188 B2 | 7/2012 | Key et al. | |
| 8,451,113 B2 | 5/2013 | Mazar et al. | |
| 8,917,173 B2 | 12/2014 | Beaudry | |
| 9,439,734 B2 | 9/2016 | Beaudry | |
| 2005/0021369 A1 | 1/2005 | Cohen et al. | |
| 2005/0033124 A1* | 2/2005 | Kelly | G06F 19/3418 600/300 |
| 2005/0246092 A1 | 11/2005 | Moscatiello | |
| 2006/0055552 A1* | 3/2006 | Chung | B60R 25/00 340/686.1 |
| 2007/0232867 A1* | 10/2007 | Hansmann | G16H 40/67 600/300 |
| 2008/0266174 A1 | 10/2008 | Medina Herrero | |

OTHER PUBLICATIONS

"Cisco Wireless Control System Configuration Guide", Jul. 9, 2010, Chapter 16: Alarms and Events, pp. 625-647, XP055270466, Retrieved from the Internet: URL:http://www.cisco.com/c/en/us/td/docs/wireless/wcs/7-0/confi-guration/guide/WCS70cg.pdf.

"Cisco Wireless Control System Configuration Guide", Software Release 7.0, Cisco Systems, Inc., Jun. 2010, 16 pgs.

Australian Examination Report No. 1 for Application No. 2012326078, dated Jan. 7, 2016, 3 pages.

European Office Action for Application No. 12841989.2, dated May 10, 2016, 5 pages.

International Search Report and Written Opinion for PCT/US2012/060870, dated Mar. 29, 2013.

Supplementary European Search Report for Application No. 12841989, dated May 13, 2015, 10 pages.

Canadian Office Action for Application No. 2851373, dated Jun. 1, 2018, 3 pages.

Extended European Search Report for Application o. 18180448.5, dated Aug. 8, 2018, 15 pages.

European Office Action for Application No. 18180448.5, dated Jan. 11, 2021, 14 pages.

Hodnebrog, Gjermund, et al., "Seamless Hand-over Algorithm for Wireless Enterprise Networks", May 29, 2007 (May 29, 2007), XP055496012, Retrieved from the Internet: URL:https://brage.bibsys.no/xmlui/bitstream/handle/11250/137092/Report_ikt590_gr14.pdf?sequence=1 &isAllowed=y [retrieved on Jul. 30, 2018].

Wifitech@conxx.Net: "how signal is affected", Dec. 16, 2009 (Dec. 16, 2009), XP055496078, Retrieved from the Internet: URL:https://community.ubnt.com/ubnt/attachments/ubnt/airMAX-General/20290/1/attenuation.pdf [retrieved on Jul. 30, 2018].

* cited by examiner

METHOD AND SYSTEM FOR DETECTING LOCATION OF FIXED WIRELESS ASSET IN A HOSPITAL ENVIRONMENT

CROSS-REFERENCE TO RELATED APPLICATIONS

This application is a continuation application of U.S. patent application Ser. No. 16/036,739 filed Jul. 16, 2018 which claims the benefit of priority under 35 U.S.C. § 120 from U.S. patent application Ser. No. 15/255,852 filed Sep. 2, 2016, now issued as U.S. Pat. No. 10,022,201, which claims the benefit of priority under 35 U.S.C. § 120 from U.S. patent application Ser. No. 14/579,355 filed Dec. 22, 2014, now issued as U.S. Pat. No. 9,439,734, that claims benefit of priority under 35 U.S.C. § 120 from U.S. patent application Ser. No. 13/277,033 filed Oct. 19, 2011, now issued as U.S. Pat. No. 8,917,173, from which are incorporated herein by reference in their entirety.

BACKGROUND

Field

The present disclosure is related to the field of medical device inventory and tracking. Specifically, the present disclosure relates to arrangements and methods for detecting location of a fixed wireless asset in a hospital environment.

Description of the Related Art

The last few years have seen explosive growth in the use of wireless communication in homes and businesses. This includes hospitals where it is increasingly advantageous to link diagnostic equipment and data access devices, such laptops, tablets, and personal data assistants (PDAs), to central data systems. In order to provide wireless connectivity, many hospitals are deploying wireless networking systems that cover most if not all areas where care is provided. A typical wireless network will have one or more wireless access devices that are connected to the network with physical cables. A hospital installation may have a number of wireless access devices positioned around the facility, each wireless access device covering an area that is determined in part by the layout and construction of the building around the wireless access device.

Hospitals are also coming under increased pressure to contain costs. One effect of this pressure is a need to maintain a current inventory of assets, such as the wireless access devices that are a part of the hospital infrastructure, as well as knowledge of the location of the assets.

SUMMARY

Locating the various components of a computer network can be a challenge for the network administrators as it may be possible to communicate with a component over the network without having any knowledge of the physical location of the device. This is particularly important for wireless access devices as their physical location determines the coverage provided within the building, and dead spots are a common problem. It is not uncommon for a wireless access device to be moved, for example to cover a former dead spot, without the new location being noted in the system records. With the deployment of mobile devices, for example a monitoring device worn by a patient, where it is desirable to track the location of the mobile device and the patient within a hospital, knowledge of the physical location of wireless access devices has become even more important. Manually tracking or, in some cases, searching for a wireless access device is difficult and time-consuming. It is desirable to be able to automatically determine the location of wireless access devices in a hospital environment.

Wireless access devices are referred to using a variety of terms such as "ports," "access points," and "gateways." Wireless communication devices may have a variety of functions related to the routing, buffering, and processing of communication signals and may be referred to as "bridges," "hubs," "routers," or "switches." For the purpose of the present disclosure, the term "fixed wireless asset" (FWA) is used to refer to any wireless communication device that is attached to a communication network, recognizing that a FWA may be relocated or is attached to a piece of equipment that may be periodically relocated such that the physical location of the FWA is not necessarily permanently fixed, but is usually stationary at a given physical location.

The present disclosure includes systems and methods adapted to determine the location of FWAs within a hospital using patient location information routinely gathered in a healthcare environment. In certain configurations, a patient is associated with an FWA and the FWA is determined to be near the location of the patient, based on the patient location information from a hospital Admission-Discharge-Transfer (ADT) database.

Certain embodiments of a system are disclosed that comprises at least one fixed wireless asset (FWA) having an asset tracking number, and at least one mobile device wirelessly coupled to the at least one FWA via a first communication link. The at least one mobile device is assigned to a person and configured to provide data to the at least one FWA. The system also includes a database comprising information associating the person with a location, and a computer coupled to the at least one FWA via a second communication link and to the database. The at least one FWA is configured to forward to the computer the data received from the at least one mobile device along with the FWA's asset tracking number. The computer is configured to receive the data and asset tracking number from the at least one FWA and retrieve the information from the database. The computer is further configured to determine the location of the at least one FWA based at least in part on the data received from the at least one FWA and the information retrieved from the database.

In certain embodiments, a system for locating a FWA within a hospital is provided. The system comprises a plurality of FWAs having respective asset tracking numbers, a database comprising associations of a plurality of patients having patient IDs with respective identified rooms in the hospital, and at least one personal care device (PCD) configured to wirelessly communicate with at least one FWA. The PCD has been assigned to one of the patients. The PCD is configured to provide to the FWA at least the patient ID of the patient to whom the PCD is assigned. The system also includes a computer that is coupled to the plurality of FWAs and to the database via a communication network. The FWAs are configured to provide at least the data received from the PCD along with the asset tracking number of the FWA providing the data. The computer is configured to receive from the FWA the data and asset tracking number and retrieve from the database at least the patient room association for the patient identified in the data received from the PCD. The computer is further configured to determine the location of at least one of the FWAs based on the patient ID received from the PCD, the asset tracking number of the FWA, and the patient room association retrieved from the database.

In certain embodiments, a method of determining a location of a FWA in a hospital environment is disclosed. The method includes the step of receiving, by a computer, at least one message from the FWA that comprises a patient ID and an identification of a PCD that is paired with the patient. The method also includes the step of receiving, by the computer, patient-room information comprising the patient IDs of a plurality of patients admitted to the hospital and identification of the hospital rooms that are assigned to the patients. The method also includes the step of determining, by the computer, the location of the FWA based on the at least one received message and the patient-room information.

In certain embodiments, a computer-readable medium having computer-executable instructions stored thereon for execution by a processor to perform a method of determining a location of a FWA in a hospital environment is disclosed. The method includes the steps of receiving at least one message from the FWA that comprises a patient ID and an identification of a PCD that is paired with the patient, receiving patient-room information comprising the patient IDs of a plurality of patients admitted to the hospital and identification of the hospital rooms that are assigned to the patients, and determining the location of the FWA based on the at least one received message and the patient-room information.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The following description discloses embodiments of systems and methods for determining the location of FWAs in a hospital or healthcare facility. In certain embodiments, the system includes a mobile apparatus that communicates wirelessly with the FWA as well as with a database that contains information about the association of patients with FWAs and the location of patients in the hospital.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. The systems and methods disclosed herein are discussed in the context of a hospital that admits patients for treatment. Nothing herein should be interpreted to limit the coverage of the claims to a healthcare environment or to medical treatment unless specifically stated as such.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Figure 1:
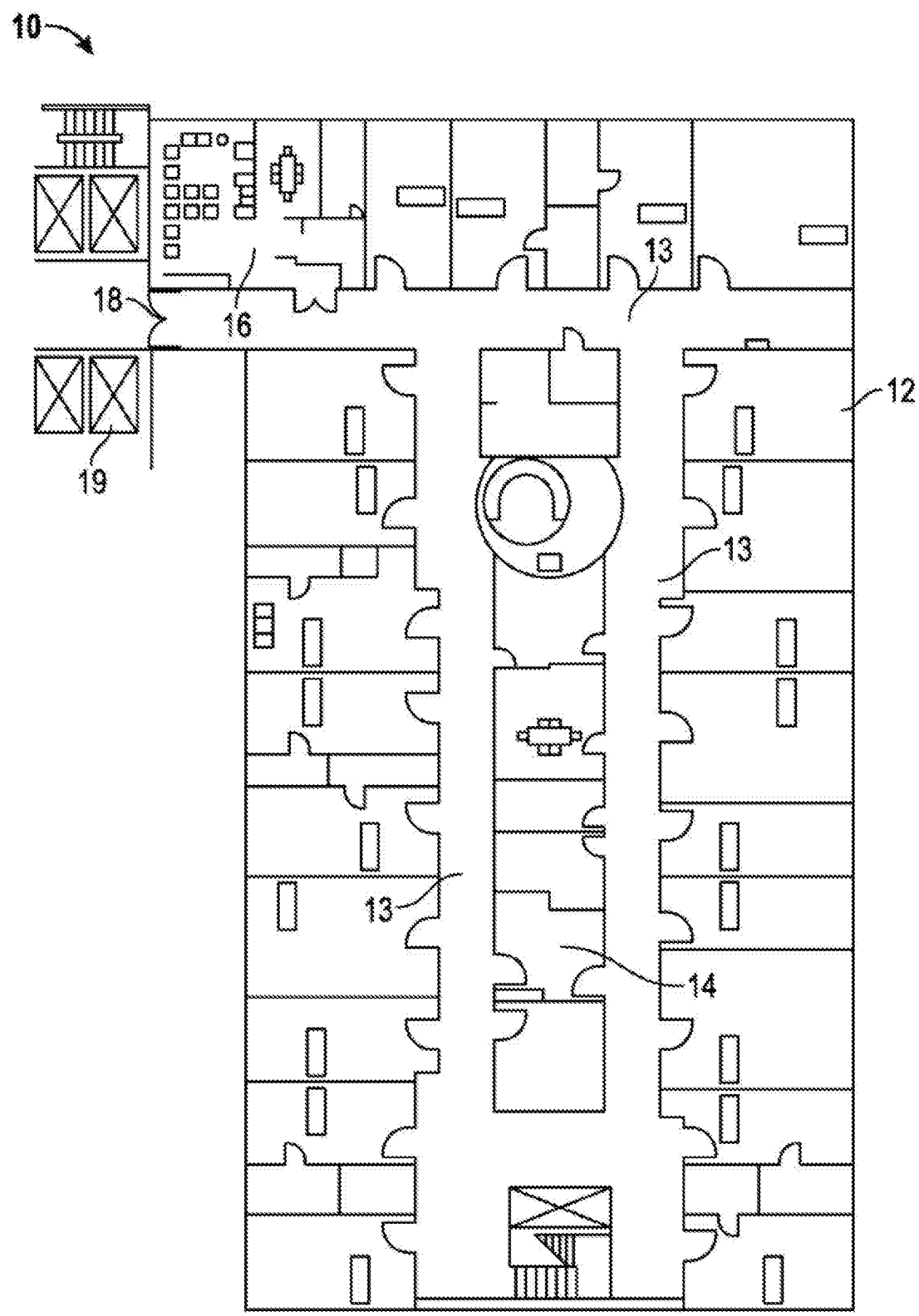
FIG. 1 is an example floor plan for a hospital care area.

FIG. 1 is a simplified example floor plan 10 for a hospital care area. In this example, numerous patient rooms 12 are located along corridors 13. Patient care rooms 14 are provided in the central area to allow for procedures that may require equipment (not shown) that is not provided in the patient rooms 12. A patient lounge 16 is located at one end of hallway 13 for patients to visit with their families or for patients to relax outside their rooms 12. Elevators 19 are located at one end of a corridor 13 that is separated from the care area by doors 18.

Providing wireless coverage for the example floor plan 10 may require multiple FWAs, depending on the power and function of the FWAs. In certain systems, it is desirable to have each FWA cover a very limited area, such as a single patient room 12, so that the physical location of a mobile device, such as an intravenous (IV) pump, may be determined to be within a certain area using the knowledge of which FWA is in communication with the mobile device and the physical location of the FWA. In such a system, each patient room 12 may have a FWA that is associated, in a database, with that particular patient room 12. When a patient is admitted to the hospital and assigned to a room, or discharged from the hospital, or moved from one room to another within the hospital, this information is stored in the hospital's ADT system. Some patient rooms 12 are configured to be occupied by a single patient while other patient rooms 12 may be configured to be shared by two or more patients.

Other FWAs may be located in public areas such as the patient lounge 16 or above the entrance doors 18. It may be possible to determine that a wirelessly equipped mobile device is in the lounge 16 or passing through the entrance doors 18 based on a wireless connection being established between the mobile device and the FWA in that location.

Figure 2:
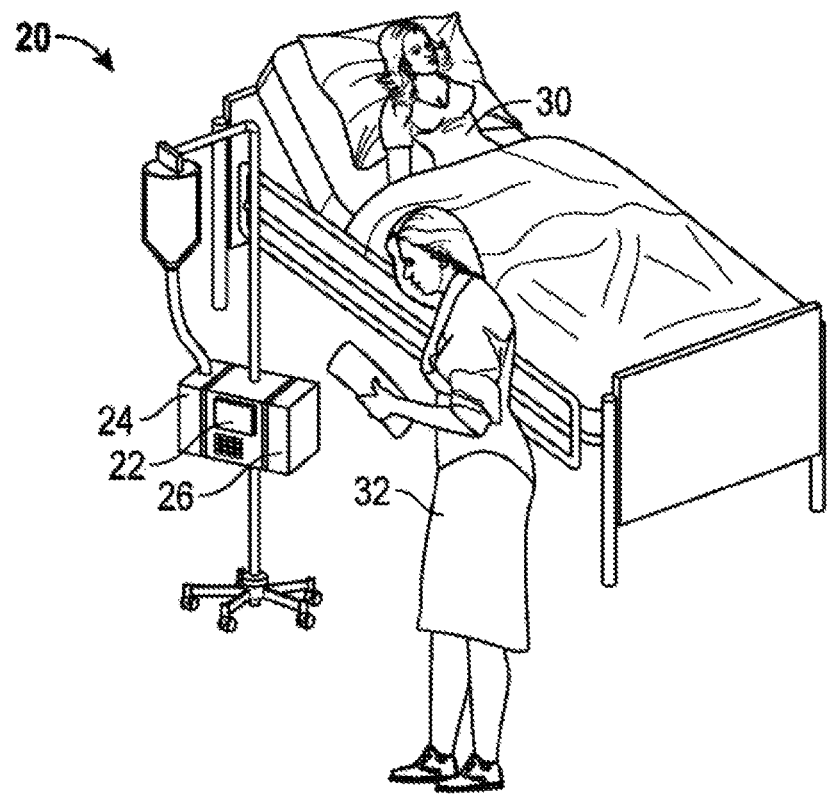
FIG. 2 illustrates a wirelessly equipped mobile medical treatment device.

FIG. 2 illustrates a wirelessly equipped mobile medical treatment device. In this example, the device is an IV system 20 that includes, in this embodiment, a control unit 22, a pumping unit 24, and a monitoring unit 26, such as a saturation of peripheral oxygen ($SpO_2$) monitor module. The control unit 22, in this example, is equipped with a wireless communication capability so that, for example, readings from the $SpO_2$ module can be uploaded regularly to a central database. In use, a caregiver 32 will associate, or "pair", the IV system 20 with a patient 30 using any of the commonly known methods of identifying the patient 30 and IV system 20, e.g. scanning a barcode attached on a wristband of the patient 30 or attached to the IV system 20, and uploading this to a hospital data system (not shown in FIG. 2) so that uploaded data can be stored in the records associated with the proper patient 30. In certain embodiments, identification of the patient is provided by other methods, such as manual data entry, selection of a patient's name from a pre-entered list, and scanning of a radio frequency identification (RFID) tag worn by the patient. This association of the IV system 20 with the patient 30 is recorded in the hospital data system.

Figure 3:
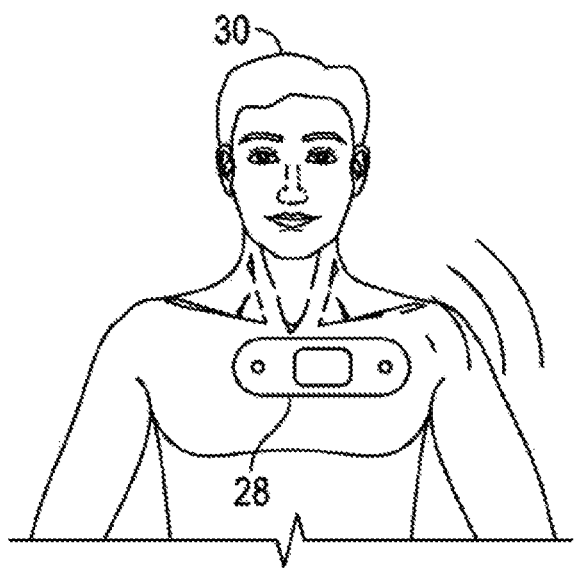
FIG. 3 depicts an embodiment of a wireless medical monitor being worn by a patient.

FIG. 3 depicts an embodiment of a wireless medical monitor 28 being worn by a patient 30. This monitor 28 is attached to the skin of the patient 30 in a manner similar to a large adhesive bandage. The monitor 28 is equipped with wireless communication capability so that a physiological attribute, for example pulse, is monitored regularly while the patient 30 moves about the hospital. The monitor 28 is associated with the patient 30 at the time that the monitor 28 is initially attached to the patient such that the uploaded monitoring data can be stored in the records associated with the proper patient 30. This association of the monitor 28 with the patient 30 is also recorded in a hospital data system. Other examples of monitors 28 can be used with embodiments of the present disclosure.

Figure 4:
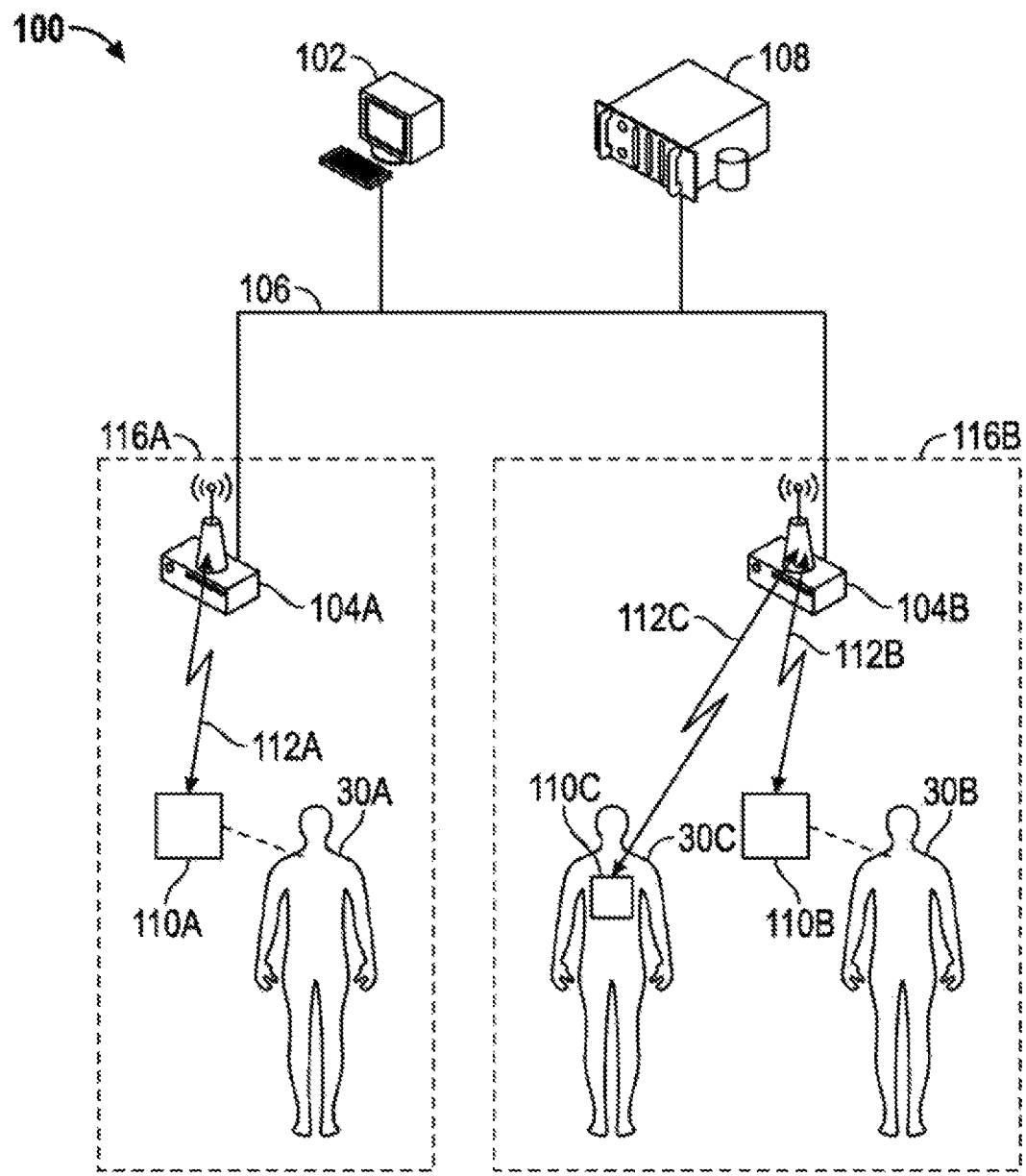
FIG. 4 is a block diagram representation of a patient care system according to certain aspects of this disclosure.

FIG. 4 is a block diagram representation of a patient care system 100, in accordance with certain configurations disclosed in the present disclosure. A computer 102 is communicatively coupled via a hospital network 106 with one or more FWAs 104A, 104E located in a respective hospital area (e.g., a patient room) 116A, 116B. An ADT database 108 is also communicatively connected to the computer 102 via the hospital network 106. Each FWA 104A, 104E is also communicatively coupled with one or more patient care devices (PCDs) 110A, 110B, 110C via a wireless communication link 112A, 112B, 112C. Each PCD 110A, 110B, 110C is respectively associated with a patient 30A, 30B, 30C. When the FWAs 104A, 104B are configured such that their range of wireless communication is limited to the respective room 116A, 116B, then it can be inferred that, for example, patient 30B is currently in the same room as FWA 104B when the PCD 110B that is associated with patient 30B is in communication with FWA 104B. In certain embodiments, FWA 104A is removed and the range of FWA 104B extended to cover room 116A with some reduction in the precision of the knowledge of the location of the detected PCDs.

Still referring to FIG. 4, while the computer 102 and the database 108 are depicted as two different blocks, it is understood that these devices can be implemented on the same hardware/software platform or can be implemented on multiple hardware/software platforms. The computer 102 is, for example, may be located at a central information technology (IT) facility in a hospital or at a nurse's work area. Similarly, the database 108 may be located at a central facility or at a business office in a hospital. The communication network and links 106 and 112 may be implemented using any of several well-known communication technologies. In certain configurations, proprietary communication technologies may also be used. For example, in certain configurations, the hospital network 106 is an Ethernet network and the communication link 112 uses an 802.11 wireless channel and protocol. In certain configurations, the communication link 112 uses a proprietary communication technology. The hospital network 106 is a wireless or a wired network, in different embodiments, or some combination of wired and wireless networks.

The present disclosure anticipates that the FWA 104 is not stationary throughout the duration of use. For example, a caregiver may move the FWA 104 during or between patient care sessions. In certain configurations, the FWA 104 is a battery-operated device, making it relatively simple for a caregiver to transport the FWA 104 to another place. In certain configurations, the FWA 104 is connected to the hospital network 106 with a plug-in cable that connects to a wall port, making it an easy task to unplug the FWA 104 and reconnect the FWA 104 to the network 106 using a different wall port.

Figure 5:
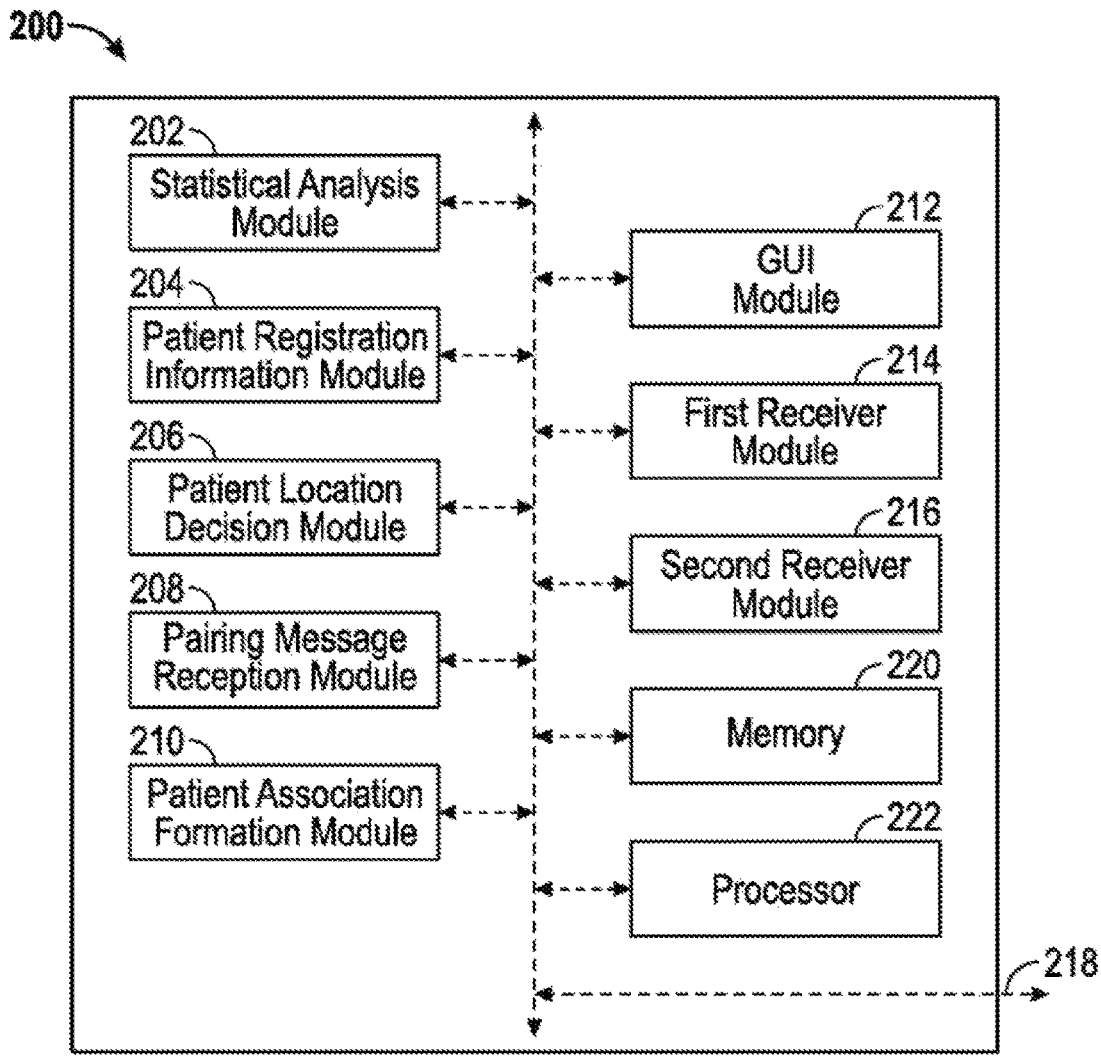
FIG. 5 is a conceptual block diagram of a computer according to certain aspects of this disclosure.

FIG. 5 illustrates a simplified conceptual block diagram of the computer 102 in accordance with certain aspects disclosed in the present disclosure. The computer 102 comprises a statistical analysis module 202, a patient registration information module 204, a patient location decision module 206, a pairing message reception module 208, a patient association formation module 210, a graphical user interface (GUI) module 212 that may include a display (not shown) and one or more data entry devices (not shown) such as a keyboard and a mouse, a first receiver module 214, a second receiver module 216, a memory 220, and a processor 222. The computer 102 is communicatively coupled with the hospital network 106 via a network interface 218. The modules can be implemented in hardware in certain embodiments. The statistical analysis module 202 is configured to determine what conclusions can be made about the location of a FWA based on messages received from a PCD 110. The patient registration information module 204 handles exchanges of information with the database 108 as described in greater detail with respect to FIG. 7. The patient location decision module 206 is configured to determine the location of the patient based on information retrieved by the patient registration information module 204. The pairing message reception module 208 is configured to associate the PCD 110 with a patient 30 based on information received from the PCD 110 and, in certain embodiments, other sources such as the GUI module 212. The first receiver module 214 is configured, in this example, to communicate over a wireless link to the PCD 110. The second receiver module 216, in this example, is configured to communicate through the network interface 218 over a hardwired link to the network 106 and therethrough to other devices such as the database 108.

In certain embodiments, the modules can be implemented in software, or a combination of hardware and software.

In certain embodiments of the computer 102, the memory 220 comprises a nonvolatile machine-readable storage medium, such as a magnetic hard disk. In certain embodiments, the memory 220 comprises a removable nonvolatile machine-readable storage medium such as an optical disk such as a Compact Disk (CD) or Digital Video Disk (DVD), or a nonvolatile storage device such as a flash drive or a magnetic storage device (e.g. a magnetic disk). In certain embodiments, the memory 220 comprises a volatile memory such as a magnetic Random Access Memory (RAM) that is configured to be used for storing temporary data or other intermediate information during execution of instructions by processor 222. In certain embodiments, the processor 222 comprises start-up instructions that instruct the processor to retrieve further instructions from the memory 220 upon start-up.

Figure 6:
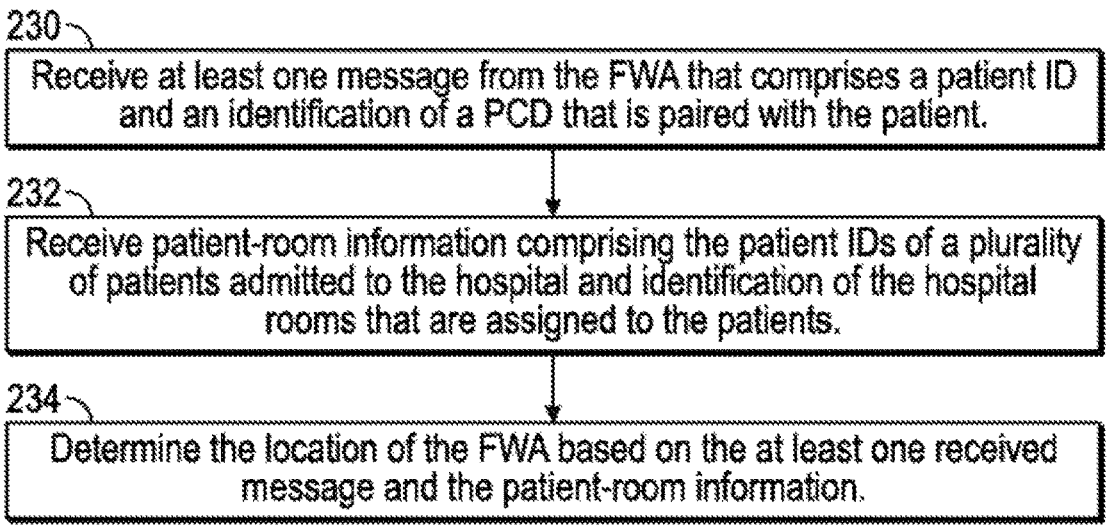
FIG. 6 is a flow chart illustrating an exemplary method of detecting the location of a fixed wireless asset in accordance with certain aspects of this disclosure.

FIG. 6 is flow chart illustrating an example of an operation of detecting a location of a given FWA 104. At operation 230, the first receiver module 214 receives at least one message from the FWA 104 that comprises a patient ID and an identification of a PCD 110 that is paired with the patient 30. At operation 232, the second receiver module 214 receives patient-room information comprising the patient IDs of a plurality of patients 30 admitted to the hospital and identification of the hospital rooms 12 that are assigned to the patients 30 and passes this information to at least one of the patient registration information module 204 and patient location decision module 206. At operation 234, the statistical analysis module 202 determines the location of the FWA 104 based on the at least one received message and the patient-room information. These operations are described in greater detail with respect to FIGS. 8A-8D.

Figure 7:
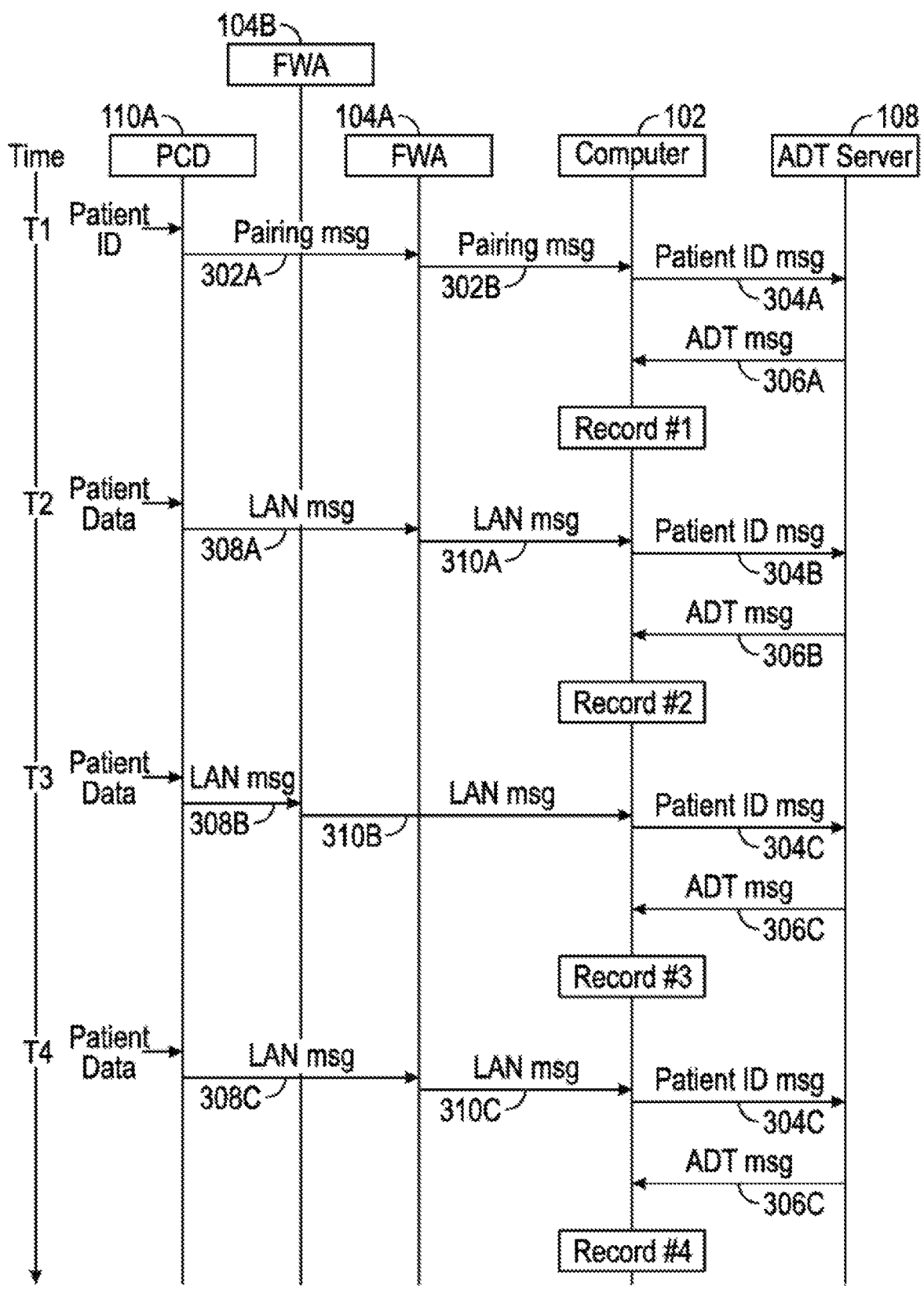
FIG. 7 is a timeline illustrating exemplary messages exchanged among various elements of the patient care system 100 according to certain aspects of this disclosure.

FIG. 7 is a timeline illustrating exemplary messages exchanged among various elements of the patient care system 100 according to certain aspects of this disclosure. The elements of FIG. 7 are those shown in FIG. 4. At time T1, prior to using the PCD 110A, for example an IV pump 20 as illustrated in FIG. 2, to perform a patient care task for a specific patient 30A, a caregiver 32 pairs the PCD 110A with the patient 30A. i.e. assigned the PCD 110A to patient 30A. In the example of FIG. 7, the caregiver 32 performs the pairing operation by entering a patient IDentifier (ID) into the patient care device 110, e.g. by scanning a barcode that is printed on a wristband worn by patient 30A using a barcode scanner module of the PCD 110A. In certain embodiments, the caregiver 32 enters the patient identification information manually into the PCD 110A. In the example of FIG. 7, PCD 110A is in communication with FWA 104A, which is located in the room assigned to patient 30A. The PCD 110A sends a pairing message 302A to the FWA 104A which, in this example, modifies the message to add an asset tracking identifier assigned to FWA 104A, and sends a pairing message 302B on to the computer 102 through the network 106. In certain embodiments, the caregiver 32 enters the patient identification information and the identification of the PCD 110A into a data entry device (not shown) that sends the information to the computer 102.

In the example of FIG. 7, the pairing messages 302A, 302B comprise: (1) an identity of the PCD 110A, e.g. an asset tracking identifier assigned to the PCD 110A, (2) a patient ID, e.g., an alphanumeric identifier assigned to the patient 30A during admission, and (3) a date-time stamp indicating when the pairing occurred.

Upon receipt of pairing message 302, the computer sends a patient ID message 304A to the database 108 requesting the currently assigned room for patient 30A. In this example, the patient ID message 304A contains (1) the patient ID received in the pairing message 302, and (2) the date-time stamp from the pairing message 302. The ADT 108 retrieves the room number that was assigned to patient 30A at the date and time indicated in patient ID message 304A. The ADT 108 sends an ADT message 306A to the computer 102 with the assigned room. In certain embodiments, the ADT message 306A includes other information such as the patient ID, the date-time stamp, and other data that enables the computer 102 to associate this ADT message 306 with the particular FWA 104A. The computer 102 then generates a data record, shown as record #1 in the example of FIG. 7, that records at least the date & time, the asset tracking identifier assigned to FWA 104A, and the room number assigned to patient 30A. In certain embodiments, the record contains the patient ID for patient 30A.

As the PCD 110A operates while the patient 30A is in the hospital, the PCD 110A establishes contact with the nearest FWA as the patient 30A moves about the hospital. At the same time, PCD 110A is, in the example of FIG. 7, accumulating data related to the patient 30A. The PCD 110A periodically sends data messages, shown as a Local Area Network (LAN) messages in FIG. 7, related to the accumulated patient data to the FWA with which the PCD 110A is currently in communication. In FIG. 7, at time T2, PCD 110A is in communication with FWA 104A and the PCD 110A sends a LAN message 308A to FWA 104A. FWA 104A adds asset tracking identifier assigned to FWA 104A and sends a LAN message 310A to the computer 102. The computer 102 sends a patient ID message 304B, which is identical in content to patient ID message 304A in this example, to the database 108. The ADT database 108 returns an ADT message 306B, which is identical in content to ADT message 306A in this example, to the computer 102. The computer 102 generates a record, shown as record #2 in FIG. 7, that includes the date & time, the asset tracking identifier assigned to FWA 104A, and the room number assigned to patient 30A.

In the example of FIG. 7, at time T3 the patient 30A is in a different room in the hospital, for example the lounge 16 of FIG. 1, and PCD 110A is in communication with a different FWA 104B. The PCD 110A sends a LAN message 308B to the FWA 104B, which adds its own asset tracking identifier to the message and forwards it as LAN message 310E to the computer 102. As before, the computer 102 sends a patient ID message 304C to the ADT server, which returns an ADT message 306C. The computer 102 creates record #3 that, because the LAN message came through FWA 104B, contains the asset tracking identifier of FWA 104B.

At time T4, patient 30A has returned to his room and therefore the PCD 110A is again in communication with FWA 104A. As before, PCD 110A sends a LAN message 308C to FWA 104A, which adds its asset tracking identifier to the message and forwards it as LAN message 310C to computer 102. The computer 102 again exchanges messages 304D, 306D with the ADT sever 108 and creates record #4 that contains the asset tracking identifier of FWA 104A.

It is understood that the operation of "bridging" or "forwarding" performed by a FWA can be performed at any layer of the network protocol stack, as is well understood in the field of computer communication. For example, in certain configurations, the FWA 104 receives a patient data-monitoring message encapsulated in an internet protocol (IP) packet from the patient care device 110 over an 802.11 communication link and forwards the received IP packet over an Ethernet link to the computer 102. In certain configurations, the FWA 104 changes the header portion of the received IP packet.

As previously described with respect to FIG. 5, the first receiver module 214 of the computer 102 is configured to receive the LAN messages 310 (as an example of LAN messages 310A, 310B, and 310C of FIG. 7 and other similar messages) and perform a determination of the location of the FWA 104A. The patient association formation module 210 of the computer 102 is able to make an association between a patient 30 and the received LAN message 310 based on the identification of the patient 30 and/or the PCD 110 conveyed in the received LAN message 310. In certain configurations, a LAN message 310 directly, or explicitly, includes an identity of the PCD 110A that sent the message and an identity of the patient 30A within the bits conveyed by the LAN message 310 itself. In certain configurations, the computer 102 receives a LAN message 310 that includes an identity of the PCD 110A that sent the message, but does not explicitly include an identity of the patient 30A. However, the computer 102 identifies the patient 30A associated with the LAN message 310 using a previously received pairing message 302B pairing the PCD 110A and the patient 30A. If the received LAN message 310 does not explicitly or directly include any identification of the PCD 110 or the patient 30, the patient association formation module 210 may still able to determine the identities using certain information in the LAN message 310, such as an IP header or a source ID of the PCD 110.

The analysis performed by computer 102 to determine the location of a FWA 104 includes analyzing one or more of timing attributes, patient information attributes and transmission attributes of the received LAN messages 310. In certain configurations, the accuracy of the estimated location of an FWA 104 is improved by comparing multiple LAN messages 310. In certain embodiments, the analysis is performed over all messages received within a predetermined time window. The time window is, for example, a contiguous period (e.g., 1 to 7 days) prior to determination of the location of the FWA 104. Alternatively, the time window may comprises multiple non-contiguous portions. In certain configurations, only LAN messages 310 received between the hours of 10 pm and 6 am, when patients 30 are typically asleep in their rooms, are considered. In certain configurations, the time window excludes visiting hours or lunch hours, during which time patients 30 may be mobile within the hospital.

As an example, in one configuration only LAN messages 310 received between the hours of 10 pm and 6 am within the last 5 days and only since the PCD 110A was associated with patient 30A are considered. The computer 102 retrieves all of the records received within the last 5 days. The computer discards all records that include the patient ID of patients not patient 30A, outside the designed time period, and prior to the date and time of the pairing message 302. In certain embodiments, the computer 102 counts the number of instances wherein the room number is the same and determines that FWA 104 is located in the room with the highest count. In certain embodiments, the computer 102 looks at the time sequence of room numbers and determines the room number of the last continuous string of instances. In certain embodiments, the computer 102 evaluates only a determined number of the most recent records.

As a second example, all LAN messages 310 received within a period of time from PCD 110A are considered regardless of which patient was associated with the PCD 110A during that time. Utilization of records from previous patients may increase the statistical accuracy if multiple patients are shown to be mapped to the same location.

In certain embodiments, the FWA is known to cover portions of multiples rooms, i.e. 30% of the area of a first room, 25% of a second adjacent room, and 35% of a third room as well as some portion of the hallways around these rooms. In this circumstance, the FWA reports only that a device is in the area around of the three rooms and does not specify a specific room.

In certain embodiments, the FWA 110 determines other attributes of the received LAN messages 308, such as a signal strength of the received LAN message 308 or a round-trip-time of the message received from a PCD 110 at the FWA 104 whose location is being determined. These capabilities are discussed in greater detail with respect to FIGS. 8A-8D.

FIGS. 8A-8D are plots of signal strength and time of receipt for messages received from a PCD 110 by a FWA 104 according to certain aspects of this disclosure. It should be noted that the scenarios for these plots are not limiting but merely examples discussed to highlight certain aspects of the analysis performed by the statistical analysis module 202. In the plots of FIGS. 8A-8D, time linearly increase along the horizontal axis and the vertical axis represents a received signal strength at the FWA 104 of LAN messages 308 from one or more PCDs 110. Each LAN message 306 corresponds to a respective LAN message 308 received at the computer, as shown in FIG. 7. LAN messages 308 received with the time window 400 are used in the analysis described herein. In these examples, signals are received from PCDs associated with patients 30A and 30B who are in different locations, i.e. not in the same room.

Figure 8A:
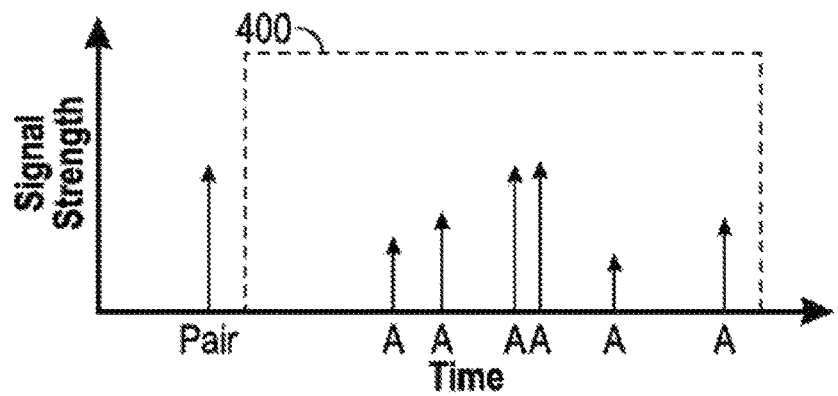
FIGS. 8A-8D are plots of signal strength and time of receipt according to certain aspects of this disclosure.

FIG. 8A depicts an example wherein the computer 102 receives a pairing message 302 before the time window 400. The computer 102 receives LAN messages 310 corresponding to LAN messages 308 that received within time window 400 by a FWA 104A from a PCD 110A associated with patient 30A, and therefore designated as "A" messages. In certain configurations, the statistical analysis module 102 draws the conclusion that the FWA 104A is located in proximity of where the corresponding patient 30A is located. As previously discussed, the location of the patient 30A is obtained from the patient location decision module 206.

Figure 8B:
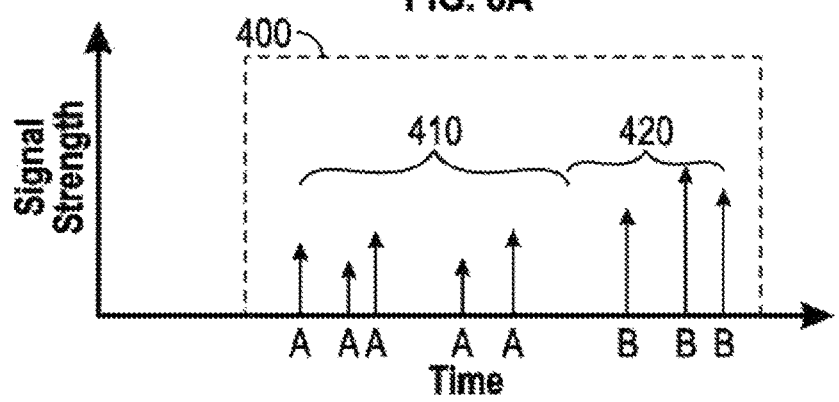

FIG. 8B illustrates another example where a first group 410 comprises received LAN messages 308 corresponding to patient 30A, followed by a second group 420 comprising received LAN messages 308 corresponding to patient 30B. Further, as depicted, the average received signal strength corresponding to the group 420 is greater than that of the group 410. In certain configurations, a "most frequently received" criterion is used and because a greater number of LAN messages 308 are received in the first group 410, the FWA 104 is determined to be in the vicinity of patient 30A. In certain other configurations, a "most recently received" criterion is used, whereby the FWA 104 is decided to be in the vicinity of patient 30B because the second group 420 was more recently received than the first group 410.

Still referring to FIG. 8B, in certain configurations, a weighted average is used to make a determination that the FWA 104 is "in the proximity of patient 30A and patient 30B." In certain configurations, the weighting is based on, for example, the numbers of received LAN messages 308 in the first and the second groups 410 and 420. In certain configurations, the weighting is based on a time elapsed since the last LAN message 308 was received corresponding to a patient 30. In certain configurations, the weighting is based on the ADT information related to patients 30A and 30B. For example, for the scenario depicted in FIG. 8B, if ADT information indicates that patient 30A was discharged after the last message in the group 410 is received, and patient B was admitted to the same hospital room, then LAN messages 308 received for patient 30A are given equal weight as those for patient 30B.

Figure 8C:
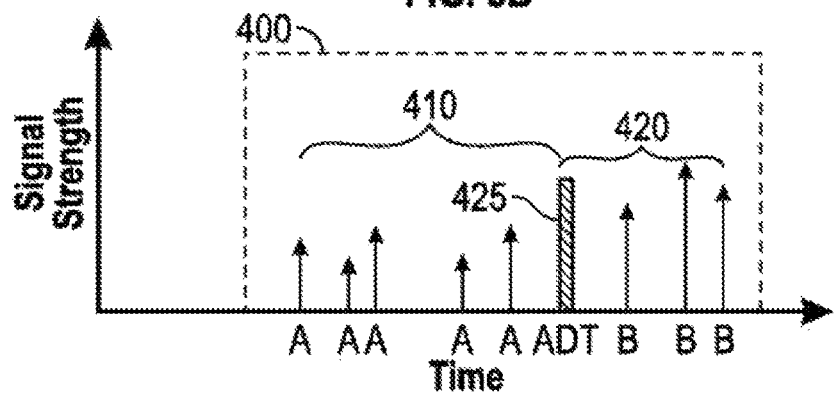

FIG. 8C depicts a scenario similar to the scenario depicted in FIG. 8B, except that an ADT event 425 indicates that patient 30A was transferred to another location within the hospital, e.g. from a recovery unit to a long-term-care unit, occurs during the time window 400. In certain configurations, because patient 30A was transferred away from the FWA 104A, the LAN messages 30 of group 410 are given zero weight.

Figure 8D:
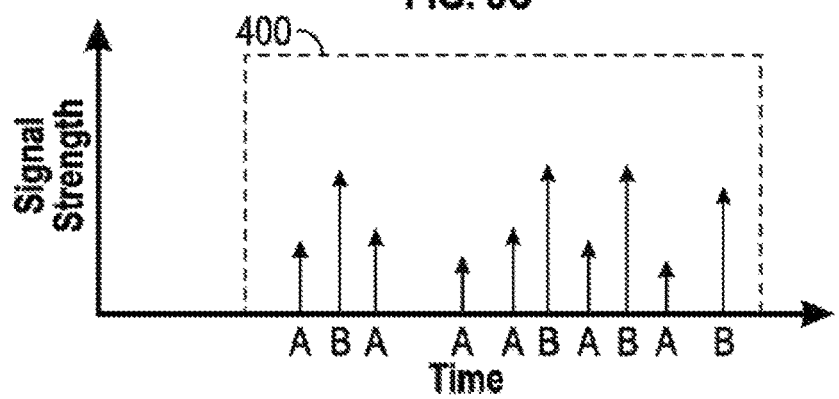

FIG. 8D depicts a scenario in which the computer 102 receives LAN messages 310 corresponding to both patients 30A and 30B over the duration of time window 400. As depicted in FIG. 4D, the LAN messages 308 corresponding to patients 30A and 30B have different signal strengths and are received at different times. In certain embodiments, when a mix of LAN messages 308 corresponding to multiple patients is received by a single FWA 104, the statistical analysis module 202 performs additional steps to calculate on a measure of the received signal strength at the FWA 104.

For example, a query is made by the computer 102 to the FWA 104 to report the received signal strengths for the LAN messages 308 received from the PCDs 110A and 110B respectively associated with patients 30A and 30B. In certain configurations, the statistical analysis module 202 determines that the FWA 104 is near the patient corresponding to the highest received signal strength. In certain configurations, the statistical analysis module 202 ignores LAN messages 308 with a received signal strength below a pre-determined threshold.

Still referring to FIG. 8D, in certain configurations, the FWA 104 is capable of performing a round-trip delay estimation for the wireless communication links 112 between the FWA 104A and the PCDs 110A and 110E that are communicating with the FWA 104A, thereby estimating the distance of the PCDs 30A, 30B from the FWA 104A. In certain configurations, when the received LAN messages 308 include a mix of LAN messages 308 corresponding to multiple patients, the computer 102 inquires the round-trip delay information from the FWA 104. In certain configurations, the statistical analysis module 202 ignores LAN messages 308 with a round-trip delay that is longer than a pre-determined threshold. i.e. farther from the FWA 110A that a predetermined distance.

In certain configurations, the statistical analysis module 202 communicates with the GUI module 212 and presents results of analysis to a user. The GUI module 212 is configured to allow a user to set certain rules of analysis. For example, the GUI could present a set of information of which PCD communicating with which FWA with less than a specified time delay, i.e. within a certain distance of that FWA, which may assist in locating an active PCD. In certain configurations, the GUI module 212 allows a user to set one or more of (1) a value of the time window 400 (e.g., 2 days or 12 hours, etc.), (2) a weighting option (e.g., equal weights or assigning higher weight to the most recent LAN messages 308, and so on), (3) a signal level threshold, the received messages below which are ignored, (4) whether to use round-trip delay values in determining a location of the FWA 104, (5) types of ADT messages (e.g., transfer information) to consider when weighting the received LAN messages, and so on.

The term "computer-readable medium" as used herein refers to any non-volatile medium that participates in providing instructions to a processor for execution. Common forms of computer-readable media include, for example, a magnetic floppy disk, a magnetic or optical hard disk, magnetic tape, a Compact Disk (CD), a Digital Video Disk (DVD), a Programmable Read-Only Memory (PROM), an Erasable Programmable Read-Only Memory (EPROM), and a flash memory device.

It will be appreciated that the methods and systems presented herein provide solutions for tracking locations of wireless devices used in many environments, particularly in patient care systems in healthcare facilities. Healthcare facilities often do not have the resources or the expertise to continually track the deployed devices throughout the healthcare facility. Adding to the difficulty is the fact that many devices are relatively portable and during use, these devices are simply hand-carried by a healthcare professional and placed at a suitable location in a healthcare facility. Healthcare professionals are often pre-occupied with other important patient care tasks and may not immediately update a database at the healthcare facility with the new location of the fixed wireless asset. The methods and systems disclosed herein enable tracking of fixed wireless assets using patient location information, which is routinely gathered by healthcare systems as a part of patient care.

Those of skill in the art would appreciate that the various illustrative blocks, modules, elements, components, methods, and algorithms described herein may be implemented as electronic hardware, computer software, or combinations of both. Furthermore, these may be partitioned differently than what is described. To illustrate this interchangeability of hardware and software, various illustrative sections, blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims.

Reference to an element in the singular is not intended to mean "one and only one" unless specifically so stated, but rather "one or more." Unless specifically stated otherwise, the term "some" refers to one or more.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "operation for."

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A system for locating a fixed wireless asset (FWA) within a medical facility, the system comprising:
 a database comprising associations of a plurality of patients having patient registration information with respective identified rooms in the medical facility; and
 a computer coupled to a plurality of FWAs and to the database via at least one communication network, wherein the computer is configured to:

receive, from an FWA included in the plurality of FWAs, a message including patient registration information and an asset tracking number of the FWA;

retrieve from the database a patient-room association for the patient identified in the data; and determine a location of the FWA based on the patient registration information, the asset tracking number of the of the FWA, and the patient-room association retrieved from the database.

2. The system of claim 1, further comprising a personal care device (PCD) configured to wirelessly communicate with at least one FWA of the plurality of FWAs, the PCD having been assigned to a patient of the plurality of patients within the medical facility, the PCD configured to provide to the respective FWA the patient registration information.

3. The system of claim 2, wherein the computer determining the location of the FWA comprises evaluating only messages received from the PCD during a specific time period.

4. The system of claim 3, wherein the determined time period is limited to a time during which patients are typically in their respective assigned hospital rooms.

5. The system of claim 2, wherein the PCD comprises a module of an intravenous infusion system.

6. The system of claim 5, wherein the module comprises at least one of a control unit, a pumping unit, or a monitoring unit.

7. The system of claim 5, wherein the FWA comprises a control unit of the intravenous infusion system.

8. The system of claim 2, wherein the PCD comprises a patient monitoring device.

9. The system of claim 1, wherein the FWA comprises a control unit of an intravenous infusion system.

10. The system of claim 1, further comprising the FWA, wherein the FWA generates the message by:

retrieving, from a memory of the FWA, the asset tracking number; and combining the asset tracking number with the patient registration information.

11. The system of claim 1, wherein the FWA comprises a control unit of an intravenous infusion system.

12. The system of claim 1, further comprising the FWA, wherein the FWA generates the message by:

retrieving, from a memory of the FWA, the asset tracking number; and combining the asset tracking number with the patient registration information.

13. A system for locating a fixed wireless asset (FWA) within a medical facility, the system comprising:

a database comprising associations of a plurality of patients having patient registration information with respective locations in the medical facility; and a computer coupled to a plurality of FWAs and to the database via at least one communication network, wherein the computer is configured to:

receive, from an FWA included in the plurality of FWAs, a message including patient registration information and an asset tracking number of the FWA;

retrieve, from the database, a patient-location association for the patient identified in the data; and determine a location of the FWA based on the patient registration information, the asset tracking number of the of the FWA, and the patient-location association retrieved from the database.

14. The system of claim 13, further comprising a personal care device (PCD) configured to wirelessly communicate with at least one FWA of the plurality of FWAs, the PCD having been assigned to a patient of the plurality of patients within the medical facility, the PCD configured to provide to the respective FWA the patient registration information.

15. The system of claim 14, wherein the computer determining the location of the FWA comprises evaluating only messages received from the PCD during a specific time period.

16. The system of claim 14, wherein the PCD comprises a module of an intravenous infusion system.

17. The system of claim 16, wherein the module comprises at least one of a control unit, a pumping unit, or a monitoring unit.

18. The system of claim 16, wherein the FWA comprises a control unit of the intravenous infusion system.

19. The system of claim 14, wherein the PCD comprises a patient monitoring device.

20. The system of claim 13, wherein the location comprises a room within the medical facility for treating the patient.

* * * * *

UNITED STATES PATENT AND TRADEMARK OFFICE
CERTIFICATE OF CORRECTION

PATENT NO. : 11,123,154 B2
APPLICATION NO. : 16/752432
DATED : September 21, 2021
INVENTOR(S) : Serge Beaudry It is certified that error appears in the above-identified patent and that said Letters Patent is hereby corrected as shown below:

In the Claims

Column 13; Line 9:
Replace "of the of the" with --of the--.

Column 14; Line 20:
Replace "of the of the" with --of the--.

Signed and Sealed this
Twenty-eighth Day of June, 2022

Katherine Kelly Vidal
*Director of the United States Patent and Trademark Office*